United States Patent [19]

Ough

[11] Patent Number: 5,263,472

[45] Date of Patent: Nov. 23, 1993

[54] LARYNGOSCOPE BLADE

[76] Inventor: Yon D. Ough, 2350 E. Ridge Rd., Beloit, Wis. 53511

[21] Appl. No.: 564,375

[22] Filed: Aug. 8, 1990

Related U.S. Application Data

[63] Continuation-in-part of Ser. No. 357,976, May 26, 1989, abandoned.

[51] Int. Cl.$^5$ .............................................. A61B 1/26
[52] U.S. Cl. .................................................... 128/11
[58] Field of Search ................... 128/6, 11, 16, 19, 23, 128/200.26

[56] References Cited

U.S. PATENT DOCUMENTS

| | | | |
|---|---|---|---|
| 3,005,452 | 10/1961 | Pitman | 128/11 |
| 4,086,919 | 5/1978 | Bullard | 128/6 |
| 4,306,547 | 12/1981 | Lowell | 128/11 |
| 4,592,343 | 6/1986 | Uesher | 128/11 |
| 4,901,708 | 2/1990 | Lee | 128/11 |

FOREIGN PATENT DOCUMENTS 2105994  4/1983  United Kingdom ................. 128/11

Primary Examiner—Mark S. Graham
Attorney, Agent, or Firm—Raymond W. Campbell

[57] ABSTRACT

An improvement for laryngoscope blades is disclosed, for expanding the field of view beyond that directly visible to a person performing intubation. A small telescope is provided, preferably integral with the blade, and includes an eyepiece near the laryngoscope handle and a front lens near but below the blade tip. The telescope is adapted to expose for remote viewing through the eyepiece an additional field of view generally above and beyond the blade tip.

9 Claims, 5 Drawing Sheets

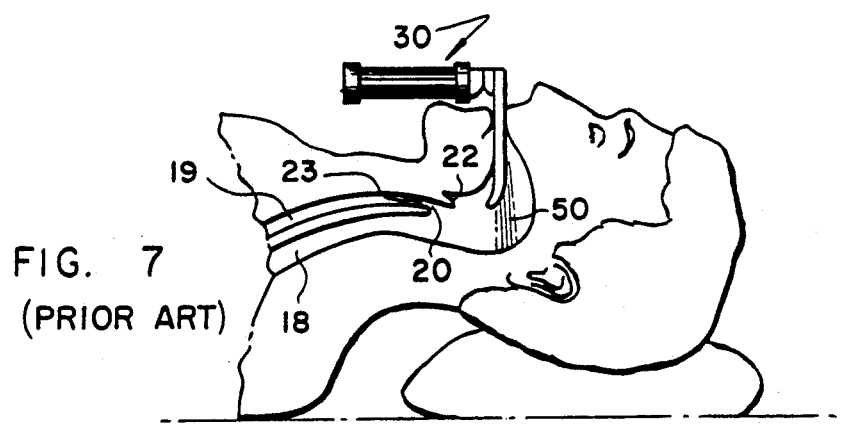
FIG. 7 (PRIOR ART)
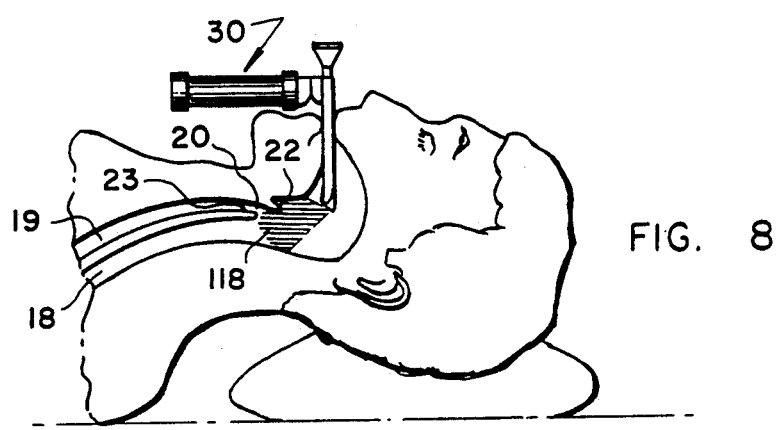
FIG. 8
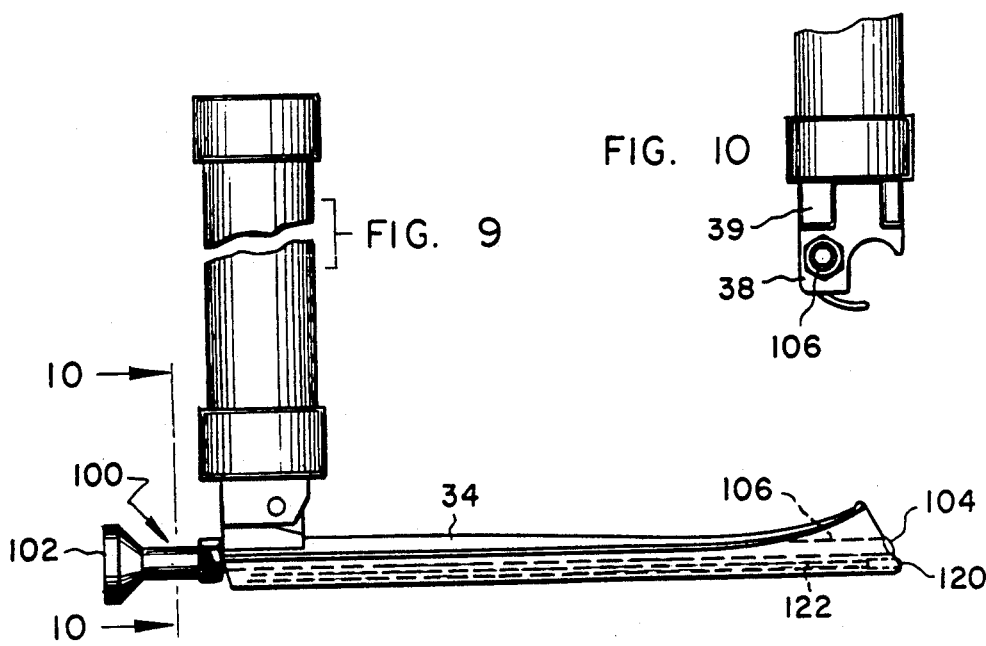
FIG. 9
FIG. 10

LARYNGOSCOPE BLADE

RELATION TO OTHER APPLICATIONS

This application is a continuation-in-part of copending U.S. application Ser. No. 07/357,976 filed May 26, 1989, abandoned for a "Laryngoscope Blade".

BACKGROUND OF THE INVENTION

Technical Field

This invention pertains generally to the field of medical instruments, and more particularly to an improved laryngoscope blade for greatly expanding the visual field presented to the medical practitioner performing endotracheal intubation.

Technical Background

During patient medical care, often it is necessary to insert an endotracheal tube for respiratory support of the patient in distress. For example, a patient under general anesthesia is unable to maintain unassisted respiration, and an endotracheal tube, which is connected to a respirator, is inserted in the patient's trachea to perform respiratory support. Endotracheal intubation also is performed frequently on critically ill patients who are unable to breathe effectively on their own, and on patients who are unable to protect their airway from vomitus from the stomach.

Endotracheal intubation procedures, which may be orotracheal wherein the endotracheal tube is inserted through the mouth of the patient, or nasotracheal wherein the endotracheal tube is inserted through the nose of the patient, are a major part of the practice of an anesthesiologist, and are performed routinely, on a daily basis. For other health care professionals, such as paramedics and other physicians, the procedure is less routine and is performed less often. For all who perform the procedure, even under ideal conditions, intubation can be highly stressful. When intubation is performed to support a non-breathing patient, brain damage or death resulting from inadequate supply of oxygen can occur within four minutes. Clearly, intubation must be completed as rapidly as possible.

During endotracheal intubation, the glottic opening, which is defined by the glottis or vocal cords and surrounding structures, must be identified, so that the tube is correctly inserted through the glottic opening and into the trachea. Positive identification of the glottic opening minimizes the possibility of esophageal intubation and the potential of hypoxic brain damage.

A laryngoscope is the instrument used to assist intubation, and typically includes a handle and detachable blade disposed at near right angle. Numerous different types of blades are available, including straight and curved types. Most practitioners tend to favor one or the other of the common blades, and will use it in the vast majority of procedures. The blade is inserted into the mouth of the patient, holding the mouth in a fully open position and the tongue against the floor of the mouth. The epiglottis frequently is elevated, either through direct contact by the laryngoscope blade or indirectly by raising hypopharyngeal tissues. Under normal circumstances, this will expose the epiglottis and glottic opening to allow direct observation by the examiner who sights along the larynqoscope blade. A light on the blade illuminates the visual field.

In perhaps one of every one-hundred patients, normal intubation becomes difficult as a result of anatomical variances. In some patients, the glottis is located anteriorly, placing the glottic opening out of the normal field of view. In other patients, such as those having small mouths or mandibular joint dysfunctions, the mouth can not be opened sufficiently for the desired positioning of the laryngoscope blade, and the field of view presented will be limited to the regions of the oropharynx. Occasionally, these conditions are anticipated, and adequate precautions can be taken. Often, however, the condition is not recognized until the intubation procedure has been started.

In a patient having elective surgery, such a condition can pose a life-threatening situation for an otherwise healthy patient. Drastic steps may become necessary to complete the procedure before brain damage or death results from oxygen deprivation. Forcing the laryngoscope blade deeper into the hypopharynx may result in excessive pressure being applied against the teeth of the patient, causing the teeth to crack or break. After beginning the procedure with standard instruments, it may become necessary to use specialized instruments to complete the procedure. Preparing and switching instruments wastes much of the limited time available for intubation, and results in even the most experienced practitioner being forced to use instruments with which he is less experienced. Further, some such specialized instruments, such as flexible fiber-optic devices, can not be used on infants because of size.

Intubation under abnormal conditions becomes highly stressful for everyone involved, including the most experienced practitioners, which may further reduce efficiency and performance.

SUMMARY OF THE INVENTION

It is therefore one of the primary objects of the present invention to provide a laryngoscope which expands the visual field presented to one performing intubation beyond that field presented for direct, unassisted observation through the mouth of the patient, and which can be used as a standard instrument during normal, day to day procedures.

Another object of the present invention is to provide on common, standard laryngoscope blades an apparatus for indirect observation of the glottic region, enabling completion of intubation under conditions in which the glottic opening can not be observed directly through the mouth of the patient.

Yet another object of the present invention is to provide a visual field expanding laryngoscope blade which is suitable for use on infants, children and adults, and which provides a panoramic view of the hypopharynx even when the patient's mouth is opened only minimally.

Still another object of the present invention is to provide a laryngoscope blade which reduces the risk of dental injury to the patient, and which reduces the risk of trauma resulting from repeated, unsuccessful attempts to complete intubation.

A further object of the present invention is to provide a laryngoscope blade which exposes for indirect observation regions above and beyond the blade tip, and which has an objective lens positioned out of the way of tissues near the blade tip.

A still further object of the present invention is to provide a laryngoscope blade which simplifies abnormal intubation procedures for both well-experienced and lesser experienced practitioners, and which simplifies intubation kits by minimizing the need for specialized equipment.

These and other objects are achieved in the present invention by providing a small telescope on various standard laryngoscope blades. The telescope includes an eyepiece in the general region of the connection between the laryngoscope handle and the laryngoscope blade, a barrel extending along and preferable integral with the blade, and a front or objective lens near the distal end of the blade. As positioned during use, the objective lens is disposed below the blade tip to avoid fouling by tissues. Suitable optical properties are provided in the telescope so that the visual field presented through the telescope includes a region generally above and in front of the telescope. One or more lights can be provided to illuminate the telescopic visual field as well as the standard visual field.

The blade can be used for standard, routine intubation procedures, and allows direct observation through the mouth similar to a standard blade of the same general type. If it becomes apparent that direct observation is inadequate for completing intubation, one performing the procedure, without changing instruments, can look through the telescope at a region not observable through direct observation. Rotating the laryngoscope can provide a panoramic view of the hypopharynx, allowing further visual examination of the region.

Additional objects and advantages of the present invention will be apparent from the detailed description and the accompanying drawings.

BRIEF DESCRIPTION OF THE DRAWINGS

FIG. 7 is a view again similar to that of FIG. 1, but showing the field of view presented in a patient whose mouth can not be opened wide.

FIG. 8 is a view of the patient shown in FIG. 7, but indicating the additional field of view presented through use of the present invention.

FIG. 9 is a side elevational view of a laryngoscope having a blade according to the present invention.

FIG. 10 is a cross-sectional view of the laryngoscope shown in FIG. 9, taken along line 10—10 of FIG. 9.

DETAILED DESCRIPTION OF THE PREFERRED EMBODIMENT

Figure 3:
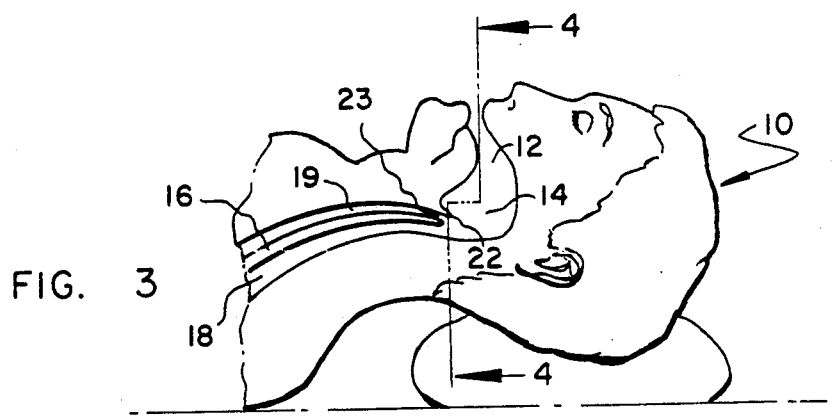
FIG. 3 is a perspective view of a patient on which certain anatomical features are identified.

Referring now more specifically to the drawings, and to FIG. 3 in particular, a patient 10 is shown, having been placed in the sniffing position in preparation for intubation. The oropharynx region of the patient is generally indicated by the numeral 12, and the hypopharynx by the numeral 14. During intubation, a tube is inserted through the nose of the patient (nasotracheal intubation) or through the mouth of the patient (orotracheal intubation) and into the trachea 16 which leads to the lungs. The tube is then connected to equipment for providing respiratory support.

Figure 4:
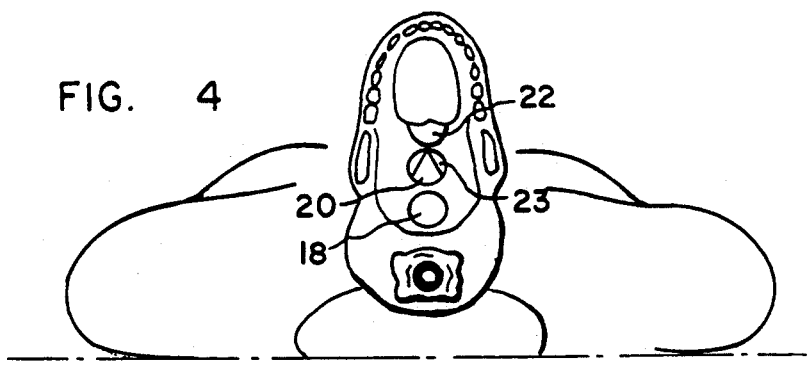
FIG. 4 is a cross-sectional view of the patient shown in FIG. 3, taken along line 4—4 of FIG. 3.

It is essential during intubation that the endotracheal tube not be inserted in the esophagus 18 which leads to the stomach, in the mistaken belief that the trachea has been located. The opening from the hypopharynx to the larynx 19 is the glottic opening, identified in FIG. 4 by the numeral 20. To distinguish the glottic opening from the esophagus which lies below it, the practitioner performing intubation looks for and identifies the epiglottis 22, a small flexible body which lies in front and above the glottis 23. Identification of the epiglottis clearly indicates the location of the glottic opening. Failure to locate and identify the glottis makes intubation a random, risky procedure.

The practitioner 24 performing intubation is positioned at the head of the patient and uses a laryngoscope 30 to aid observation of the anatomical structures and identification of the glottic opening. The laryngoscope includes a handle 32 and a blade 34. The blade 34 includes a first or Connecting end 36 having a fixture 38 for mating attachment with a complementary fixture 39 of the handle 32. Such attachments are common and well-known in the art, and will not be described in further detail herein. The blade 34 further includes a second, distal end or tip 40 which is passed through the patient's mouth and at an angle into the hypopharynx during the intubation procedure.

Figure 2:
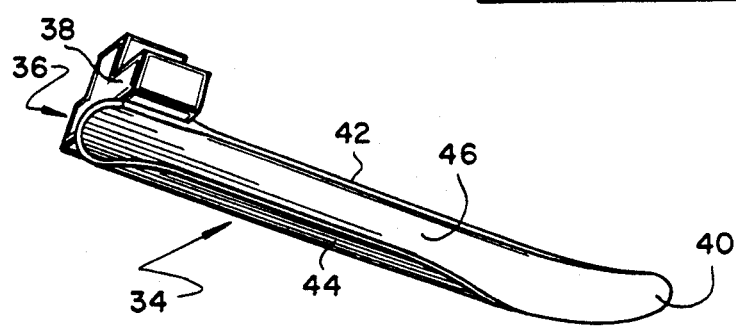
FIG. 2 is a perspective view of a laryngoscope blade of the prior art

In FIG. 2 as an enlarged view, and in other Figures illustrating the prior art, a standard, straight blade is shown, substantially illustrative of the blade embodiment commonly referred to as a Miller blade. Other common, straight blade types are known as Wisconsin, Oxiport-Miller, Schapira, Snow, Phillips, Whitehead, Eversole, Flagg, Guedel and Bennett blades. All include a substantially straight body member 42. The illustrated Miller blade has a generally flat flange portion 44 and a semi-cylindrical body portion 46 converging and terminating at the distal end 40. Others of the straight blades have varying shapes and contours, although extending generally in a straight orientation. The straight blade embodiments may be contrasted with curved blade embodiments which have a pronounced arc. Common curved blades are known as MacIntosh and Siker blades.

While a straight Miller blade is illustrated, it should be understood that the present invention works equally well with other straight blade types, and may also be adapted for use on curved blades such as MacIntosh and Siker blades. All of the blades, both straight and curved, are available in different sizes for children and adults. The present invention can be adapted for use on various size blades.

Figure 1:
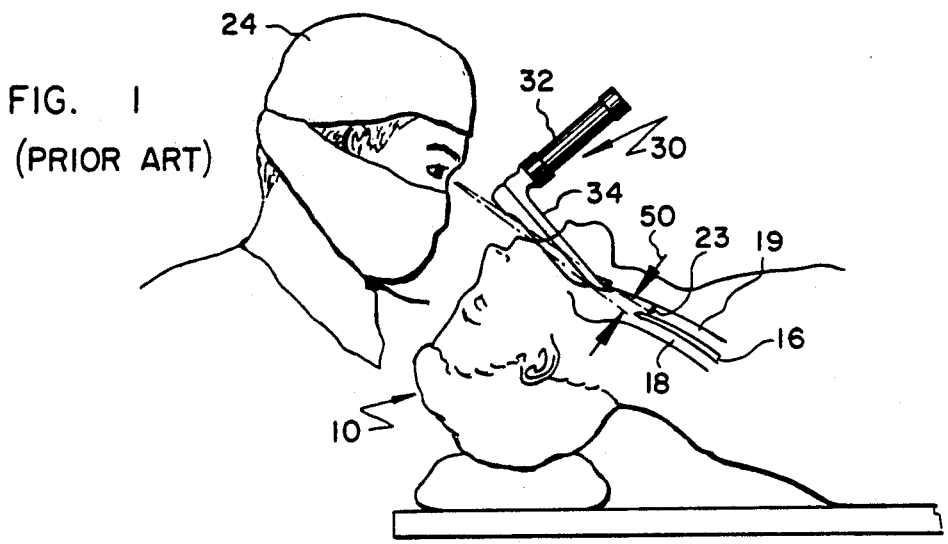
FIG. 1 is a perspective view of a patient in position for routine intubation, showing some internal anatomical structures, a laryngoscope according to the prior art positioned for intubation and a person viewing along the laryngoscope blade into the patient's mouth.

During normal intubation with a straight blade, the distal end 40 of the straight blade is used to elevate the epiglottis 22, revealing the glottic opening 20. Such normal intubation is illustrated in FIG. 1, with the general view available to the practitioner 24 by sighting through the semi-cylindrical body portion 46 along the blade 34 being illustrated by field of view 50.

Referring now to FIGS. 9 through 12, the present invention can be seen, and includes a telescope 100 connected to the blade 34. The telescope includes an eyepiece 102 disposed near the first or connecting end 36 of the blade and a front or objective lens 104 disposed at the distal end of the blade. A telescope barrel 106 extends between the eyepiece and the front lens, preferable the barrel being integral with the blade body. In the embodiment shown the telescope is disposed left of center and generally adjacent the semi-cylindrical body portion 46. The precise location of the telescope may vary depending on the design of the blade in which it is incorporated. Normally, the telescope is disposed slightly left of the midline of the blade.

The telescope may or may not provide magnification. In adults it may be adequate to provide remote, indirect viewing as will be described subsequently, without significant magnification. In children and for some specific procedures, magnification may assist the practitioner in performing intubation and in examining the hypopharynx.

Figure 13:
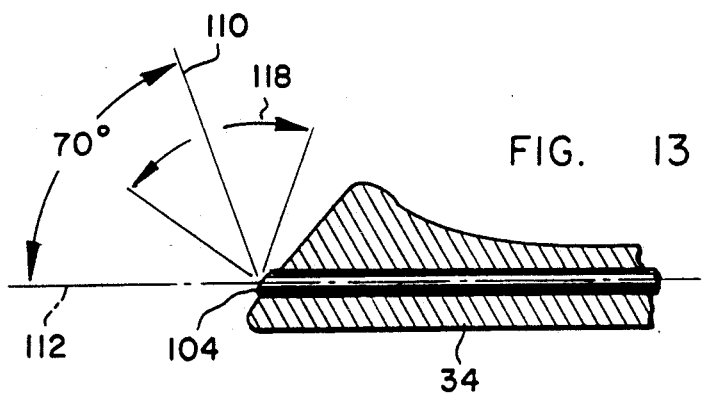
FIG. 13 is an illustration of the angle of sight or observation for a telescope used in the present invention.

The objective lens 104 is disposed and optically adapted to expose to the practitioner viewing through the telescope a region generally above of and beyond the distal end of the blade. Such small telescopes are known for use in other medical procedures such as cystoscopy, and are available with various angles of observation, including ones having center lines 110 of the telescopic field of view 118 being twelve degrees, seventy degrees and ninety degrees from a line directly in front of the telescope axis. It is believed that a telescope having at least about a thirty degree angle will be sufficient for the present invention, and a so-called seventy degree telescope is particularly useful in the present invention. The seventy degree telescopic angle of observation is illustrated in FIG. 13, with the center line of the telescopic field of view being indicated by numeral 110 and the center line extended of the telescope axis being indicated by numeral 112. The angle defined between lines 110 and 112 is approximately seventy degrees; however, other angles of sight also can be employed advantageously.

Figure 14:
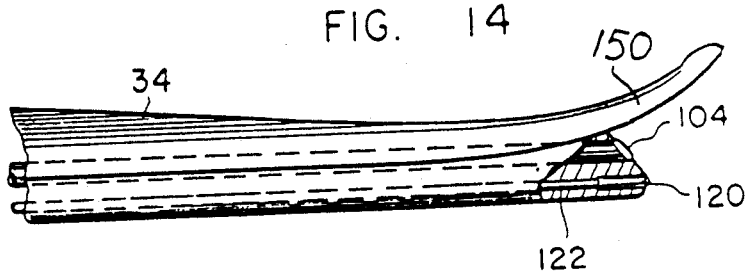
FIG. 14 is an enlarged, fragmentary view in partial cross-section similar to that of FIG. 11, but showing a second embodiment of the present invention.
Figure 15:
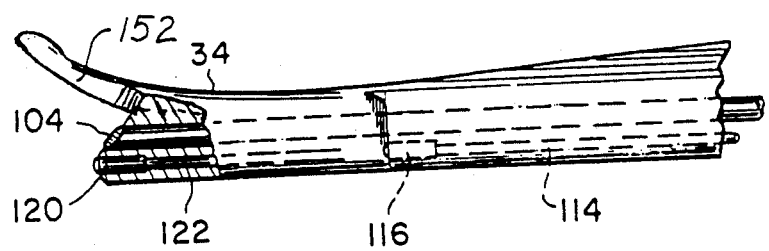
FIG. 15 is an enlarged, fragmentary view of the side opposite the side of the improved laryngoscope blade shown in FIG. 14.

The objective lens is disposed generally below the blade tip, so as not to be fouled by tissues near the blade tip. The objective lens may be in front of and below the blade tip as illustrated in FIGS. 9, 11, 12 and 13, or the objective lens may be behind and below the blade tip as illustrated in FIGS. 14 and 15. In the second embodiment, as shown in FIGS. 14 and 15, it is advantageous to modify the blade tip from the symmetric rounded tip of prior art blades to provide a notched out portion to expose the objective lens. At the left side of the blade tip, instead of the blade edge extending outwardly and rearwardly from the tip as at edge 150 on the right side, the left side edge has a segment 152 at a much smaller angle to the blade axis, or even parallel to the axis. Segment 152 extends rearwardly from the tip sufficiently far to expose the objective lens. The segment 152 defines an edge generally nearer the midline of the blade than the telescope is near the midline.

In conventional laryngoscope blades, lights are provided to illuminate the standard field of view 50. Commonly, batteries in the handle supply energy to illumination units disposed toward the distal end of the blade. While various methods of supplying and directing the light can be used, state of the art laryngoscopes utilize an optical fiber 114 and illumination unit 116 disposed along the blade length.

In the present invention, it is desirable to provide a second illumination unit 120 near the distal end of the blade to illuminate the telescopic field of view 118. A branch optical fiber 122 is extended to the illumination unit 120.

Figure 5:
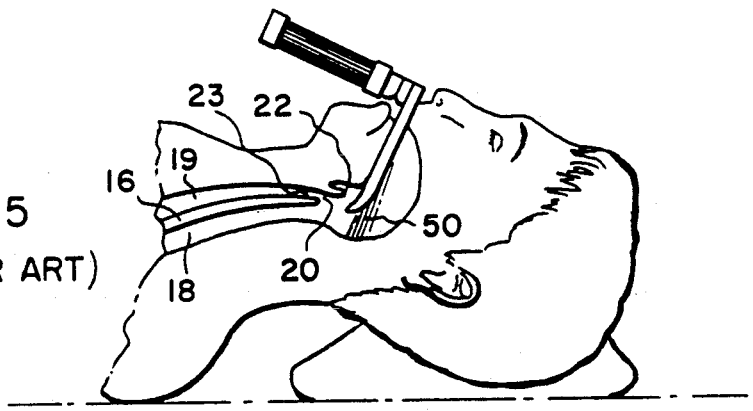
FIG. 5 is view similar to FIG. 1, but showing the field of view in a patient having a glottis of pronounced anterior location.

Advantageous use of the present invention can be seen by comparing various drawings. In FIG. 5 a patient having an anteriorly located glottis is shown. In such a situation, during attempts at intubation the standard visual field of view 50 does not include the epiglottis, glottic opening or the like. The natural tendency of one performing intubation of such a patient is to pull the end of the handle 32 toward the patient's forehead, in an attempt to expose the glottic opening. This can place excessive pressure against the teeth of the patient, even cracking or breaking them. During difficult intubations, such dental injuries are not uncommon.

Figure 6:
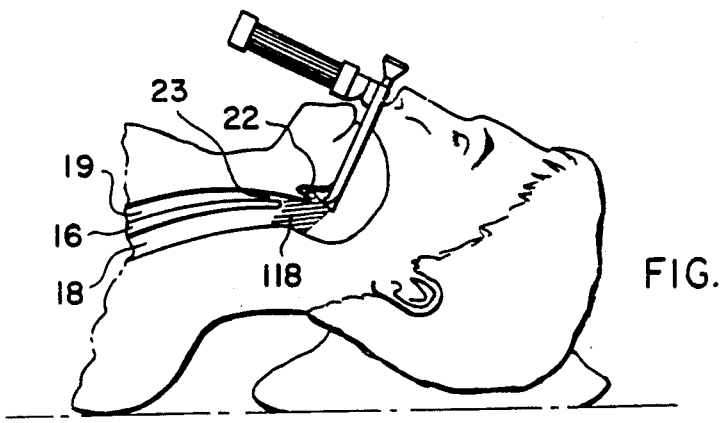
FIG. 6 is a view of the patient shown in FIG. 5, but indicating the additional field of view presented through use of the present invention.
Figure 11:
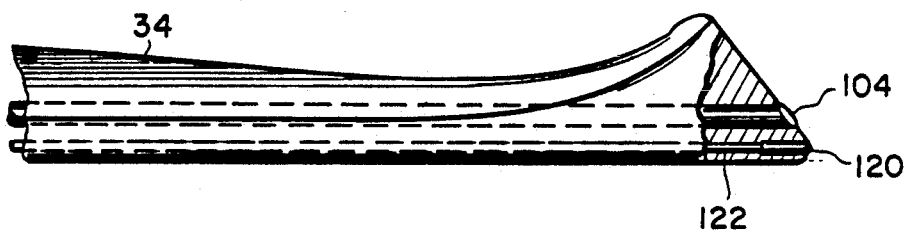
FIG. 11 is an enlarged, fragmentary view, in partial cross-section, of a laryngoscope blade embodying the present invention.
Figure 12:
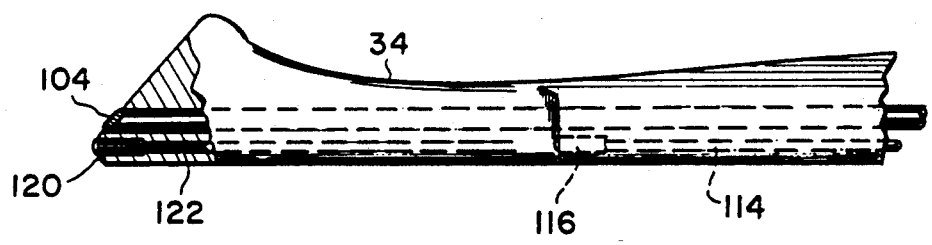
FIG. 12 is an enlarged, fragmentary view in partial cross-section similar to that of FIG. 11, but showing the side of the laryngoscope blade opposite the side shown in FIG. 11.

In FIG. 6, the telescopic field of view 118 made available by the present invention extends above and beyond the blade distal end. This expanded field of view includes the epiglottis and glottic opening. Intubation can be completed without excessively forcing the laryngoscope against the patient's teeth.

In FIG. 7, an even more difficult intubation is illustrated. Due to anatomical conditions, the patient's mouth can be opened only minimally. Without placing excessive pressure against the patient's teeth, the laryngoscope blade can be inserted only substantially straight, and not angled toward the epiglottis as required. The standard field of view 50 available when the laryngoscope is in this position does not expose the epiglottis and glottic opening.

Even under the extreme conditions illustrated in FIG. 7, the telescope assisted blade clearly exposes the epiglottis and glottic opening. The telescopic field of view 118 is again directed toward the glottic opening as shown in FIG. 8. The illumination unit 120 near the distal end of the blade provides light for completing the intubation procedure.

In the use and operation of a laryngoscope blade embodying the present invention, medical practitioners who perform intubation can use the modified blade of their choice, with telescope in place, for all intubation procedures, even when the expanded field of view presented by the telescope is not necessary. If difficulties are encountered in locating and identifying the glottic opening, the practitioner can immediately adjust to direct the examination through the telescope eyepiece, thereby availing himself or herself of the expanded field of view through the telescope. Switching from the unassisted view available by direct observation through the mouth, to the expanded telescopic view can be done quickly, without the need to change instruments or even remove the laryngoscope from the patient's mouth. This eliminates waste of time and maximizes the time available for completing difficult intubation.

The present invention reduces the risk of trauma through its ready availability and its simplicity of use.

Some practitioners may chose to use the telescopic view during normal intubation. The constant availability of the telescope allows the practitioner to periodically use the telescope even when not required, thereby maintaining a high level of skill in its use. Further, advantages of the telescope will be used more readily as a result of its availability, thereby reducing trauma resulting when the practitioner's view is obstructed and undue pressure is exerted against teeth or repeated unsuccessful attempts are made at completing intubation.

The telescope is adaptable for use on various types and sizes of blades. By minimizing the need for special, infrequently used instruments intubation kits are simplified. No unusual techniques or skills are required to use the invention except for familiarity in manipulating and inserting the endotracheal tube in coordination with an indirectly viewed field. Thus, in difficult intubation, the present invention is easier to use than other specialized instruments previously available, particularly for those who perform intubations infrequently.

Slight tilting and rotation of the laryngoscope and telescope enables the practitioner to examine the hypopharynx closely and may assist in other procedures.

While one embodiment of an improved laryngoscope blade has been shown and described herein, it should be understood that various changes may be made without departing from the scope of the present invention.

I claim:

1. An improved laryngoscope blade comprising:
   a body shaped for insertion through a patient's mouth to depress the patient's tongue during endotracheal intubation;
   said body having a connecting end adapted for connecting said blade to a laryngoscope handle, and a distal end extending into the hypopharynx of the patient being intubated, said body being shaped to elevate the epiglottis and to expose the glottic opening of the patient for direct visual observation alongside the blade during normal, routine intubation; and
   a telescope disposed along said body, said telescope including a barrel connected to said body, an eyepiece at one end of said barrel near said connecting end of said blade body, and a front lens at an end of said barrel opposite said eyepiece and near said distal end of said blade body, said front lens being disposed lower than said distal end and said front lens being at least a 30 degree lens optically adapted to expose for indirect observation regions generally above and in front of said front lens.

2. An improved laryngoscope blade as defined in claim 1 in which said front lens is disposed slightly beyond said distal end.

3. An improved laryngoscope blade as defined in claim 1 in which a light is provided for illuminating said visual field.

4. An improved laryngoscope blade as defined in claim 1 in which said front lens is disposed slightly beyond said distal end.

5. An improved laryngoscope blade as defined in claim 1 in which said front lens is disposed behind and lower than said distal end, and an edge of said blade extends rearwardly from the distal end substantially parallel to a longitudinal axis of said blade to expose the front lens.

6. In a laryngoscope having a handle and a blade connected to the handle and extending outwardly from the handle, the blade being shaped for insertion through the mouth and into the hypopharynx of a patient being intubated, the blade having a first end for connecting the blade to the handle and a distal end which in use is inserted into the patient, the improvement comprising;
   a telescope extending along the blade, said telescope having;
      an eyepiece near the handle of the laryngoscope and near the first end of the blade;
      a telescope barrel extending substantially the length of the blade and having a longitudinal axis;
      a front lens disposed near the distal end of the blade;
      said eyepiece, said barrel longitudinal axis and said front lens being in substantial linear alignment; and
      said front lens being at least a 30 degree lens optically adapted to present a visual field above and in front thereof for indirect visual observation through said eyepiece.

7. In a laryngoscope, the improvement as defined in claim 6 in which said front lens is disposed below and slightly beyond said distal end.

8. In a laryngoscope, the improvement as defined in claim 6 in which said front lens is disposed below and behind said distal end, near but alongside a longitudinal midline of the blade, and the blade distal end being shaped to expose the front lens from above the blade.

9. In a laryngoscope blade, the improvement as defined in claim 8 in which a side edge of the blade nearest said telescope extends rearwardly from the distal end of the blade substantially parallel to said midline of said blade, nearer to said midline than is said front lens.

* * * * *